US00PP08581P

United States Patent [19]

Warriner, deceased

[11] Patent Number: Plant 8,581

[45] Date of Patent: Feb. 8, 1994

[54] FLORIBUNDA ROSE PLANT NAMED 'JACSIM'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 883,309

[22] Filed: May 14, 1992

[51] Int. Cl.[5] ..... A01H 5/00

[52] U.S. Cl. ..... Plt./26

[58] Field of Search ..... Plt. 22, 26, 27

*Primary Examiner*—Howard J. Locker

*Attorney, Agent, or Firm*—Klarquist, Sparkman, Campbell, Leigh and Whinston

[57] ABSTRACT

A floribunda rose having a compact, upright and well branched growth habit. It has a high level of disease resistance and an early and rapid rebloom, and is easily propagated by budding and through softwood and hardwood cuttings.

1 Drawing Sheet

The present invention relates to a new and distinct variety of rose plant of the Floribunda class which was originated by me by crossing the variety JACjem, U.S. Plant Pat. No. 5,001, with the variety JACink, U.S. Plant Pat. No. 4,089.

The primary objective of this breeding was to produce a new rose variety having the compact growth habit and disease resistant foliage of JACjem, combined with the early and constant bloom of JACink. The objective was substantially achieved along with other desirable improvements as evidenced by the following unique combination of characteristics which are outstanding in the new variety and which distinguish it from its parents, as well as from all other varieties of which I am aware:

1. Compact upright well branched habit of growth;
2. Resistance to common rose diseases powdery mildew and rust;
3. Early and rapid rebloom of pink flowers in large clusters;
4. Ease of propagation by softwood and hardwood cuttings.

Asexual reproduction of this new variety by budding and by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACjem, U.S. Plant Pat. No. 5,001.

*Pollen parent.*—JACink, U.S. Plant Pat. No. 4,089.

Classification:

*Botanical.*—Rosa hybrida.

*Commercial.*—Floribunda.

FLOWER

Observations made from specimens grown in Somis, Calif., in test gardens from August–October, 1991.

Blooming habit: Recurrent, continuous.

Bud:

*Size.*—1" when the petals start to unfurl.

*Form.*—Short, pointed ovoid.

*Color.*—When sepals first divide, bud color is Red Group 55B. When half blown, the upper sides of the petals are Red Group 55B; and the lower sides of the petals are Red Group 55B with a distinctive light yellow (Yellow Group 8C) color on the lower third of the petal reverse.

*Sepals.*—Color: Green Group 138C. Surface texture: Covered in fine hairs. There are three normally to heavily appendaged sepals. There are two unappendaged sepals with hairy edges.

*Receptacle.*—Color: Green Group 138B. Shape: Funnel. Size: Small, ⅜"×⅜". Surface: Smooth.

*Peduncle.*—Length: Short, 2–2½". Surface: Smooth and glandular. Color: Medium green. Strength: Stiff, erect.

Bloom:

*Size.*—Medium. Average open size is 3½–4".

*Borne.*—Several together, in clusters. If in clusters: Flat.

*Stems.*—Short, 8–10".

*Form.*—When first open: High centered. Permanence: Flattens, outer petals curl back.

*Petalage.*—Number of petals under normal conditions: 20.

*Color.*—The upper side of the petals is Red Group 55B. The reverse side of the petals is Red Group 55B changing to Yellow Group 8C on the lower third of the petal reverse. The base of the petals has a small yellow half moon at the point of attachment (¼"×¼"). The major color on the upper side is Red Group 55B.

*Variegations.*—Occasional white streak on the guard petals.

*Discoloration.*—The general tonality at the end of the first day: No change. At the end of the third day: No change.

*Fragrance.*—Slight.

Petals:

*Texture.*—Thick.
*Shape.*—Round, notched.
*Form.*—Tips slightly recurved; edges slightly quilled.
*Arrangement.*—Imbricated, with a few petaloids in the center.
*Persistence.*—Drop off cleanly.
*Lastingness.*—On the plant: Fair, 4–5 days. As a cut flower: Fair, 5 days.

Reproductive parts:
*Anthers.*—Size: Medium. Quantity: Many. Color: Yellow. Arrangement: Regular around styles.
*Filaments.*—Color: Reddish brown.
*Pollen.*—Color: Gold yellow.
*Styles.*—Color: White.
*Stigmas.*—Color: Red.

Form: Bush.

Growth: Very vigorous, upright, branching, compact.

Foliage: Number of leaflets on normal mid-stem leaves: 5 or 7.
*Size.*—Medium, 5″×4″.
*Quantity.*—Abundant.
*Color.*—New foliage: Upper side is bright green with distinctive red edge with the lower side being reddish green. Old foliage: Dark green.

Leaflets:
*Shape.*—Oval pointed.
*Texture.*—Upper side: Leathery, glossy.
*Edge.*—Serrated.

*Serration.*—Single; small.
*Petiole rachis.*—Color: Green.
*Petiole underside.*—Smooth, with occasional prickles.
*Stipules.*—Medium, serrated.
*Disease resistance.*—Resistant to mildew and rust under normal growing conditions at Somis, Calif.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Hooked slightly downward.
*Color when young.*—Red.

Small prickles:
*Quantity.*—On main stalks: None. On laterals: None.

I claim:

1. A new and distinct variety of rose plant of the floribunda class, substantially as herein shown and described, characterized particularly as to novelty by the unique combination of its compact, upright and well branched growth habit, its high level of disease resistance, its early and rapid rebloom and its ease of propagation both by traditional budding and by soft and hardwood cuttings.

* * * * *

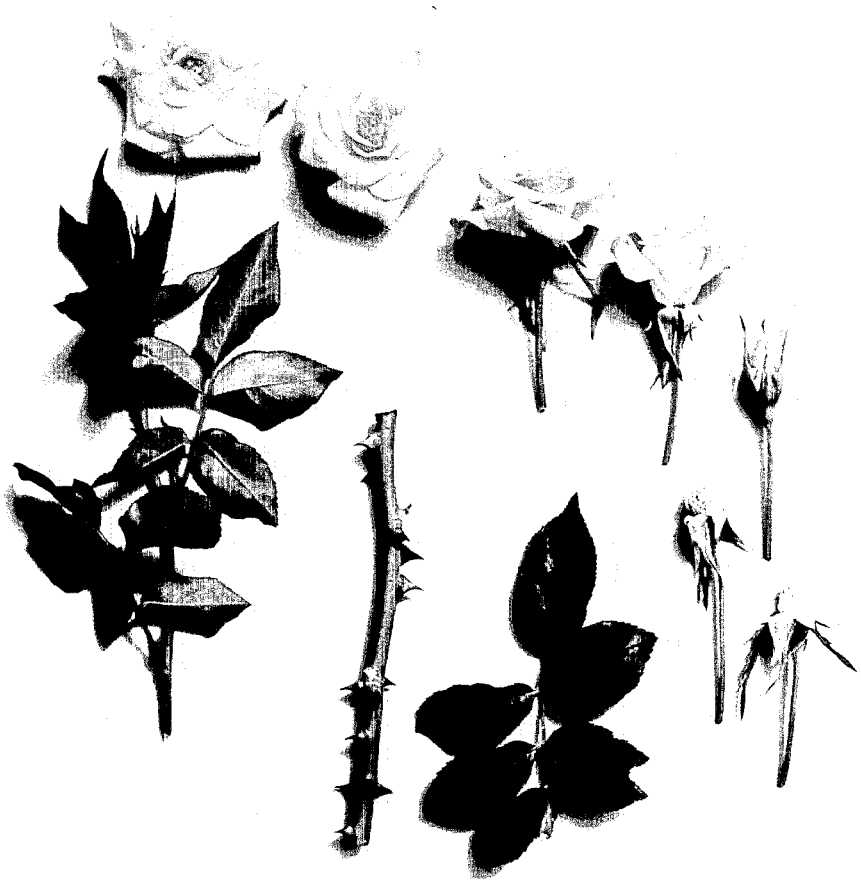
JACsim